(12) United States Patent
Epstein

(10) Patent No.: US 6,801,418 B1
(45) Date of Patent: Oct. 5, 2004

(54) GROUNDING ELEMENTS FOR ELIMINATING ESD VIA FLOOR COVERINGS AND DEVICES

(76) Inventor: Barry M. Epstein, 3 Milford Pl., Dallas, TX (US) 75230

(*) Notice: Subject to any disclaimer, the term of this patent is extended or adjusted under 35 U.S.C. 154(b) by 123 days.

(21) Appl. No.: 10/131,528

(22) Filed: Apr. 25, 2002

Related U.S. Application Data

(63) Continuation-in-part of application No. 09/934,047, filed on Aug. 22, 2001.

(51) Int. Cl.[7] .................................................. H02H 9/00
(52) U.S. Cl. ............................ 361/58; 361/200; 174/51
(58) Field of Search ........................ 361/58, 212, 220, 361/222, 816; 174/35 R, 51

(56) References Cited

U.S. PATENT DOCUMENTS

| | | | |
|---|---|---|---|
| 4,016,357 A | * | 4/1977 | Abrahamsen ................. 174/48 |
| 4,605,988 A | * | 8/1986 | Nienhuis et al. ............. 361/829 |
| 4,959,504 A | * | 9/1990 | Yarger et al. ........... 174/35 MS |
| 5,057,965 A | * | 10/1991 | Wilson ......................... 361/212 |
| 5,749,178 A | * | 5/1998 | Garmong .................... 52/79.1 |

* cited by examiner

Primary Examiner—Hung V. Ngo
(74) Attorney, Agent, or Firm—Terry M Gernstein

(57) ABSTRACT

Grounding elements are used to properly ground floor coverings and other elements whereby a floor covering, such as a carpet, need not be removed and reinstalled to correct a grounding problem. Properly grounded floor coverings and other devices reduces the effects of electrostatic discharge (ESD) and eliminates disruptive leak paths. One form of the invention has an element that is touched by a user layered on top of an ESD grounded work surface.

34 Claims, 7 Drawing Sheets

US 6,801,418 B1

GROUNDING ELEMENTS FOR ELIMINATING ESD VIA FLOOR COVERINGS AND DEVICES

CROSS-REFERENCE TO RELATED APPLICATIONS

The present application is a continuation-in-part application of patent application titled SYSTEM FOR PROTECTING A PERSON FROM THE EFFECTS OF ESD, Ser. No. 09/934,047, filed on Aug. 22, 2001, by the same inventor and currently pending and incorporates by reference the disclosure of co-pending application titled A PLUG AND CIRCUITRY FOR GROUNDING AN ELEMENT filed by the same inventor concurrently herewith.

TECHNICAL FIELD OF THE INVENTION

The present invention relates to the general art of electrical systems and devices, and to the particular field of discharging or preventing accumulation of electric charges.

BACKGROUND OF THE INVENTION

The problem of electrostatic discharge (ESD) is well known. From merely receiving a mild shock after crossing a room and touching a metal object, to sending a shock into electronic equipment, nearly everyone has experienced an ESD problem at some time.

While static electricity is extremely complex, several overall theories are generally accepted with regard to the action of ESD. Static electricity charges on a person or object are generally like charges. As such, as static electricity charges build up on a person or object, these charges tend to migrate as far apart from each other as possible as determined by the geometry of the person of object. Thus, for example, it is common for static electricity charges to migrate to a person's fingertips. For this reason, when that person reaches out to touch an electrically conductive object, a spark will jump when the gap between that person's fingertips and the object based upon the potential difference between the fingertips and the object. This discharge is very rapid and can be quite violent. If the electrically conductive object is sensitive electronic equipment, that equipment may be damaged either from the magnitude of the discharge and/or from the speed of the discharge. At the least, the charge could cause the equipment to execute an error. A sufficient number of such discharges may eventually damage the equipment.

Accordingly, the art contains many inventions intended to protect the equipment or the person from the effects of this sudden, and sometimes violent, discharge associated with ESD.

For instance, in the logging industry where chains are lowered by helicopter to loggers waiting on the ground to fasten fresh-cut timber to them so it could be airlifted to the sawmill or nearby waterway, track access point or the like, the loggers are often reluctant to grab the chain because of a painful shock that may occur as a result of a buildup of static electricity which will be discharged to ground through their bodies. This particular problem has been solved by incorporating a resistance in the line from the charge-carrying object, such as the helicopter, to the person on the ground. The high resistance causes the current to be low enough that the discharge will not be painful.

However, this is cumbersome. This solution may be even more cumbersome if the person is an office worker who moves around a great deal. Accordingly, this solution to the ESD problem has serious shortcomings.

Accordingly, there is a need for a system that protects a person against the effects of ESD but can do so in a manner that does not interfere with any task the person may be performing and further will not be cumbersome or burdensome for the person to use.

Still other inventions are directed to protecting electronic equipment from the effects of ESD. For example, many computers include touch pads or touch areas for the user to touch before touching the remainder of the computer. The touch pads are grounded so the ESD will pass from the person via a spark or the like directly to ground without going to or through the computer.

While many of these devices work well, there are several problem areas not addressed thereby. This results in drawbacks and disadvantages for such devices when a person or equipment are situated in certain environments or subject to certain conditions.

First, no matter how effective a touch pad is it will be totally ineffective if the person does not use it. That is, if the person carrying a large ESD charge forgets to touch the touch pad and proceeds to touch a computer, the ESD will discharge through the computer and the touch pad will have been useless. Thus, a shortcoming of such touch pads is that they require the person to remember to use it.

Furthermore, no matter how effective the ESD protection device is, the current level and/or the change in current level may be so high that either the person or the equipment can be damaged.

Still further, while placing a touch pad on a computer may protect the computer it does not protect the user from the effects of an electrostatic discharge.

As mentioned above, the majority of applications for the prevention of ESD are in the manufacturing or medical fields and are largely concerned with protecting the 'manufacturing' process or sensitive components for ESD damage. Examples include moving mediums such as the manufacture of rolls of paper, the assembly of delicate electronic chips and circuitry and surgeon-patient contact during an operation.

An analysis of each of the above will help illustrate the shortcomings of the prior art. In the manufacture or printing of paper, long rolls of paper may move at high speed. Often the path may involve rubber or other rollers and guides. As the paper rubs across such items a static electricity charge may be generated. Since the paper path is well controlled, it is an easy process to place grounded conductive brushes or flat metal springs in contact with the moving paper since the paper stays in a fixed path. Such electrodes are connected directly to the grounded frame of the associated machinery or to another path eventually leading to earth ground or other equalizing means.

Another common application of ESD control is in the production or repair of fragile electronics such as computer circuit boards. Even a slight electrostatic discharge through a sensitive device may destroy it. Therefore, significant effort and cost is devoted to eliminating the possibilities of electrostatic potentials in the vicinity of the sensitive electronics. Typically, a single ground point is provided that all associated elements are connected to so that no electrostatic potential can exist between them that might flow through the sensitive electronics. For example, an assembly person is connected to a ground, typically by a wrist strap tether. The tether generally consists of a wrist pad and grounding wire that is eventually connected back to the single ground point. For operator safety, the ground wire typically contains a 1 Meg resistor to limit current flow to safe levels should the operator come in contact with 120 volts AC. This tethering restraint is inconvenient and not considered suitable for a typical office worker or call center operator. The single ground point is eventually connected to true earth ground or other equalizing point by another conductor.

Applications are similar in the medical field, employing similar tethers and/or foot/shoe connectors also considered impractical for the typical office worker environment.

Today, a new set of ESD problems is emerging in the typical work place or home office environment. Today, a typical worker may exist in a virtually electrically isolated environment—a plastic computer case, plastic keyboard, plastic control knobs on a molded plastic control panel, plastic office chair with man-made fabric and plastic wheels, non-conductive flooring or carpeting and even a headset with foam or molded plastic earpieces and plastic microphone tube.

As the operator moves in his/her chair, there are many opportunities for a very large electrostatic charge to build up on his/her body. Friction between dissimilar materials is the classical means for generation of electrostatic voltages. There are many such situations that exist continually in the operator environment today—the operator's clothing sliding against the chair back or arm rests, the operator's shoes sliding on the carpet, the plastic chair wheels sliding against the carpet are a few examples. The effects can be cumulative over a long period of time, and can become quite high.

Eventually a discharge or equalization to (true earth) ground must take place. The higher the value of the electrostatic voltage charge, the greater the distance the charge may 'jump' to discharge, and the more 'catastrophic' the event to the operator. For example, there are many documented cases of operators in call centers experiencing a very loud pop or explosion in their ear, ear pain, and even bleeding in the ear as the discharge path appears to take place through the operator's headset. Other documented cases include severe neck pain, nausea, numbness, elevated blood pressure and rapid heart beat.

In an attempt to mitigate these effects, "anti static" carpet may often be installed in the initial design or construction of a workplace.

There are a number of different types of carpet intended to reduce the disturbing effects of electrostatic charge build up on a person's body. They are designed to be 'partially' electrically conductive or dissipative to reduce the effects of ESD (Electrostatic Discharge) by draining the charge from a person's body via shoes or specially worn metal heel plates which may then have a conductive strap to the person's skin. The term dissipative in ESD terminology typically refers a relatively high resistance to ground, such as 100 megohms. Although this sounds like a high value, it is effective for draining static charge as compared to many floorings, adhesives, and especially underfloorings that are considered as insulators and not effective for ESD.

Proper performance of these carpets depends on proper installation which may typically include grounding by a metal plate perhaps every 10 to 30 feet or other conductive underflooring means.

Often, the anti-static carpet appears not to work, even when samples of it test within spec. Or, it may work in part of a facility but not elsewhere. This may be evidenced by most static shocks taking place in one area of a facility. Investigation in such cases typically reveals a grounding difference between the areas. The troubled area may be an add-on area where the same carpet was ordered but the installer didn't follow instructions, or the troubled area may have an insulating plywood underfloor or raised floor that is not conductive.

Unfortunately re-installation of the carpeting is not feasible in many office environments. For example, modular office partitions may be sitting on the carpet, along with their load of wall hanging cabinets, electrical and network wiring, file cabinets, chairs, etc. Compounding the problem are the facts that office modules are usually small, further raising the density of furniture and an electrician might be needed to remove module wiring so the units could be disassembled. Thus attempting to reinstall the carpet may be almost as major as a building remodeling.

As users in the workplace become concerned about ESD, they may be sensitive to every logical source and solution. This sensitivity often focuses on certain items such as the plastic face plate covering many CRT monitors. Running a hand over the face plate may draw a static charge that may be viewed by the user as one of the sources of static electricity buildup to be concerned about.

There are many possibilities as to why these effects are worse than the typical nuisance static electricity charged walking around the house. For instance, the discharge path may be more surprising or appear worse to the user if it involves the user's ear. Recently, this has been attributed to electrostatic discharge of the operator with the grounding mechanism being the metallic portion of the ear piece coupled to its metallic conductors and eventually to earth ground through its associated electronics. This may be a direct low impedance ground or it might be a higher impedance which is still sufficiently low with respect to that needed to successfully equalize the static charge. Still in other cases, as explained below, the associated electronics may potentially make the discharge injury to the person more severe and disturbing by causing a high current pulse to take place as the discharge event.

In some cases, the associated electronics may experience physical damage or processing disturbances due to the operator electrostatic discharge. For example, the headphone circuit might involve a transformer with a 600 to 10,000 volt breakdown rating between its windings (connected to the headset diaphragm) and conductive metal core. However, the electrostatic voltage on the operator may exceed 15,000 volts-far more than the design tolerance of the transformer. Should the transformer be exposed to such excessive high voltage, a 'breakdown' or 'shorting' may occur. Thus, the operator electrostatic voltage might cause a 'short circuit' insulation breakdown or lower resistance to develop between the headset winding (secondary) and primary winding which may be at a constant high voltage level with respect to ground or the transformer core which may be connected to earth ground, thus completing the discharge path.

The transformer breakdown may cause a permanent equipment failure. Other equipment damage or errors can also occur due to the electrostatic discharge event. The electrostatic discharge event may cause an electromagnetic or radio frequency pulse to be generated. This pulse may radiate into nearby circuitry causing errors in processing or noise in audio or video circuits. Although a transformer discharge event has been described above, other similar discharge paths can be envisioned, with similar catastrophic results.

With continued miniaturization of electronics, the problems may become more severe as circuit component voltage tolerances become less and enclosure insulation distances become less.

Accordingly, there is a need for an ESD protection system that protects a person as well as sensitive electronics from the effects of ESD, even if that person is in an environment that is intended to nominally insulate that person or electronic equipment from ESD.

As the cost of doing business increases, many businesses are reluctant to purchase new original equipment. Thus, it is most advantageous if existing equipment can be easily modified or retrofit to achieve new and improved results. This is the situation with protecting people from the effects of ESD. Thus, there is a need for a system for protecting people against the effects of ESD that can easily be retrofit onto existing equipment.

When grounding ESD it is also important that a disrupting or damaging charge not be induced or superimposed back into nearby sensitive electronics. In the case of modular furniture, there may only be one ground wire present which is wired to each one of the electrical outlets located in the modular furniture. This ground wire becomes the source of ground for each and every piece of attached electronics, such as PC's at each work station all connected together in a network. The network may be extended to PC's located in various rooms or large groups. Signal voltages are very small on the network, and the network may 'follow' the ground paths. There is also resistance or impedance in any ground network. This may be especially true on grounding conductors used in modular furniture or office raceway systems since space is limited and conductors are usually just large enough to meet the minimums of the National Electric Code. Therefore, any significant ground current from ESD may be converted to a relatively high voltage as compared to signal levels. As indicated in FIG. 11A, circuitry sneak paths often exist at each connected device in a network environment between the signal paths and ground. ESD discharge currents in the ground path may generate a potential and this is a voltage that may be superimposed on the PC's and network causing disruption or damage by interfering with (relatively minute) signal voltages. By a similar process noise may be caused which is widespread into phone systems such as in a call center or cause noise in studio audio and video systems. Other similar processes will be obvious to one skilled in the art such as automation, laboratories, control centers, broadcast studios, etc.

Therefore, there is a need for a means of grounding electrostatic discharge currents for grounding equipment so that sneak paths present do not develop disturbing voltages or currents.

OBJECTS OF THE INVENTION

It is a main object of the present invention to protect a person from the effects of ESD.

It is another object of the present invention to protect a person from the effects of ESD without requiring that person to wear any cumbersome wearing apparel.

It is another object of the present invention to protect a person from the effects of ESD without requiring the person to remember to carry out any special operation.

It is another object of the present invention to prevent or reduce an uncomfortable, disturbing or harmful electrostatic discharge to a person.

It is another object of the present invention to prevent or reduce an electrostatic discharge that might interfere with a person's ability to carry out his or her job.

It is another object of the present invention to provide a system to equalize (drain or discharge) an electrostatic charge from a person in a safe, harmless, nonnoticeable or minimally noticeable manner.

It is another object of the present invention to provide a contact surface to the person that is compatible with their normal (workspace) environment and provides discharge contact in the normal course of the operator's activities.

It is another object of the present invention to minimize the static shock that may take place upon initial contact by a prior-charged person.

It is another object of the present invention to provide a carefully controlled ground discharge path.

It is another object of the present invention to provide a ground discharge path that minimizes radiated disturbances to nearby equipment.

It is another object of the present invention to provide a discharge path that minimizes conducted disturbances to interconnected equipment.

It is another object of the present invention to provide a convenient earthing or equalization means.

It is another object of the present invention to support other work necessities of the operator such as operation of a computer mouse, keyboard, track ball or similar needs.

It is another object of the present invention to provide a grounding means via an existing ground of the associated electronics limiting the discharge current to a minimal value and waveshape so the operation of the associated electronics is not degraded.

It is another object of the present invention to provide an ESD suitable grounding means via existing signal conductors of the associated electronics limiting the discharge current to a minimal value and waveshape so the operation of the associated electronics is not degraded.

It is another object of the present invention to provide a convenient connection means for retrofit or connection in the field to existing systems by an unskilled person.

It is another object of the present invention to provide a convenient means for grounding equipment so that disruptive sneak path currents are not created.

It is another object of the present invention to provide a system for grounding electrostatic discharge current for grounding equipment so that any sneak paths present do not develop disturbing voltages or currents.

It is another object of the present invention to prevent equipment damage or operational disruption due to ESD from a person.

It is another object of the present invention to provide a system that will protect a person from the effects of ESD and which can be used in connection with an electrical plug.

It is another object of the invention to provide a means of grounding anti-static carpet or other applicable flooring materials without requiring upheaval of the workplace.

It is another object of the invention to provide a means of grounding anti-static carpet or other applicable flooring materials without requiring deinstallation and reinstallation of the carpeting.

It is another object of the invention to provide a means of grounding anti-static carpet or other applicable flooring materials by using file cabinets, desks, modular office partitions, other equipment, or the carpet itself to aid in providing sustained mechanical contact for grounding purposes.

It is another object of the invention to provide a means of grounding anti-static carpet or other applicable flooring materials in a safe manner should AC volt such as 120 volts be present.

It is another object of the invention to provide a means of grounding anti-static carpet or other applicable flooring materials to selected ground sources to achieve single point (equipotential) grounding with other office equipment.

It is another object of the invention to provide a means of grounding anti-static carpet or other applicable flooring materials with large surface area contacts commensurate with surrounding objects.

It is another object of the invention to provide a means of grounding anti-static carpet or other applicable materials insulated from random grounds or other objects.

It is another object of the invention to provide a means of grounding anti-static carpet or other applicable materials such that nearby sensitive electronic equipment is not disturbed by conducted or radiated emission as ESD takes place.

It is another object of the invention to provide a means of reducing the electrostatic charge perceived to build up on CRT display monitors.

It is another object of the invention to provide an ESD protection system that protects sensitive electronics from the effects of ESD, even if the equipment is in an environment that is intended to nominally insulate that electronic equipment from ESD.

It is another object of the present invention to provide an ESD protection system that can be easily used with existing equipment.

It is another object of the present invention to provide an ESD protection system that can be used in a layered format.

SUMMARY OF THE INVENTION

These and other objects are achieved by a system which augments the grounding of a flooring system such as anti-static carpet without the trauma of reinstallation of the carpet. Reinstallation can be a major problem, especially if the carpeting is covered with tens or even hundreds of modular workstation cubicles complete with file cabinets, PC's, etc.

Grounding is provided by conductive surfaces in intimate contact with the carpeting. The conductive surfaces are configured to be compatible with the surroundings and in such cases to use other objects as weights to enhance the conductor/carpet contact.

The conductive surface may be insulated as needed to avoid contacts with unwanted grounds. A circuit connects the conductive surface to the desired ground. This may be a plug arrangement as defined in a copending application. Circuitry may be included for safety against AC voltage shock and to prevent radiation or current during ESD from disturbing sensitive electronics.

Optional grounding of CRT monitor face plates which often harbor a static charge is provided in a similar manner.

It is noted that for purposes of this disclosure, the word conductive will be used to refer to the electrostatic discharge contact area being discussed in the general sense unless otherwise noted. In the true sense of the ESD definition that term means all but insulators. In the strict ESD discussion, conduction typically refers to resistances of 0 to 0.1 megohm, dissipative typically refers to 0.1 megohm to about $10^{12}$ ohms, and above that as insulative or non-conductive. A combination of two or more of the following is provided: convenient personnel contact means, current limiting means, and grounding path are provided. The current limiting means may contain series elements of high resistance and/or inductance. The inductance is to limit the development of radiated or conducted high frequency, high impulse leading edges of current or voltage which may upset or damage nearby or connected electronics. The high series resistance further limits total current to a value such that static electric charges are not significant if superimposed upon logic or logic ground conductors. The high resistance also limits current flow to the user if instead of ground the ground wire comes in contact with a high voltage source. The value of resistance can be quite high since the goal is merely to reduce the static charges to low levels (for example 500 volts or less) on a periodic basis of minutes or hours as the charge is built up. However, the large resistance prevents a person from receiving a shock if they have a charge when they initially contact the contact element. That is, the large resistance is a balance between actually connecting a contact point to a grounding circuit (which would provide a path for a walk-up shock to occur) and preventing a walkup shock by "isolating" the contact device from the grounding circuit. Points of contact to the user are designed to be those that the user touches continually or intermittently in the normal course of operation so that bleeding of ESD can occur on a continual basis. Examples may include conductive mouse pads, conductive elements on the surface of a computer mouse or computer keyboard, trackball, conductive knobs or elements on a mic mixing panel, conductive elements on the headband or earpieces of a headset worn by the user, often used controls or touch points on virtually any type of user-operated equipment. A convenient earthing means is provided to drain off the static current so the charge may be effectively equalized.

If discharge methods are not used, the static discharge might build up for minutes or hours reaching very high values. The eventual uncontrolled discharge might take place in the user's ear to the metallic diaphragm inside the earpiece. The event may be frightening to the user.

BRIEF DESCRIPTION OF THE DRAWING FIGURES

FIG. 4A is a foot to be placed under an element such as furniture or the like.

FIG. 4B is a foot having floor covering engaging elements to be placed under an element such as furniture or the like.

FIG. 5 is an insulated foot to be placed under an element such as furniture replacement or a foot in modular partitions or the like.

DETAILED DESCRIPTION OF THE PREFERRED EMBODIMENT OF THE INVENTION

Figure 1A:
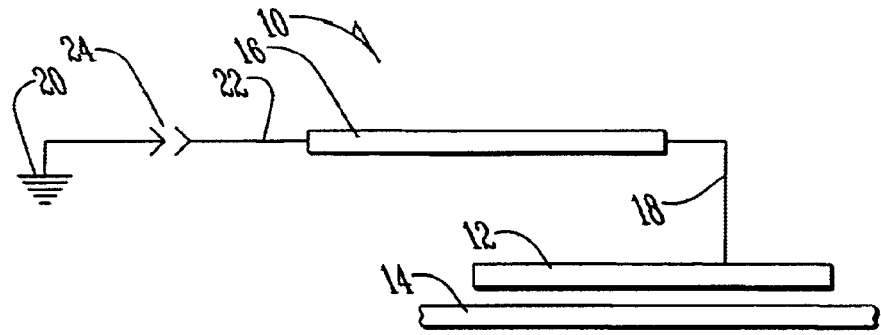
FIG. 1A is a circuit illustrating the basic system concept of the system embodying the present invention.

Other objects, features and advantages of the invention will become apparent from a consideration of the following detailed description and the accompanying drawings.

The build up of static charge on an individual generally takes place over time in many workplace environments. It may occur due to continued friction between shoes and carpet, clothing and chair, etc. Thus for protection it is necessary to provide a means of contact to a person's bare skin that is both casual and frequent during the work shift. Research and experience indicates that this should be every few minutes or so. Most individuals do not feel a discharge shock of 2000 volts or less and experience indicates that voltages may be building to the 5000 volt, 10,000 volt or more range before breakdown occurs. Generally, the operator is at his/her work position for an hour or more before the breakdown occurs.

Such breakdown may be considered as potentially disturbing to both the person and equipment, far more so than the typical nuisance discharge experienced when walking across a carpeted floor in the winter and touching a door knob. For example, there are cases of shock experienced when reaching for the "mute" button on an operator's telephone or from the user's ear through the metal parts of a headset worn by the operator.

There are many documented cases of this last occurrence requiring paramedic attention for weakness, blurred vision, high blood pressure, increased heartbeat, etc. There appears to be two reasons why this is more severe than the typical doorknob shock: (1) the electrostatic buildup may take place for a long time before breakdown occurs and hence be of greater magnitude than the typical carpet charge; (2) if discharge occurs at the ear, the associated sound may appear very loud to the operator, further adding to the perceived severity of the shock.

Generally the minimum discharge voltage a person can perceive is about 2000 volts. For purposes of this discussion an electrostatic voltage of 10,000 volts is assumed as a walk up initial voltage when first touching the ESD protective mat and is the voltage that will be used in the following discussion.

In many workplace applications historically metal grounded surfaces have been used so a zero resistance to ground is common and considered safe. However, the initial walk up discharge shock in such a case can be very significant and disturbing. The shock is significant because significant electron flow takes place due to the obviously large number of electrons available in the earth for neutralization. A similar shock also takes place when touching large metal objects because of the large number of electrons available in the object for discharge. This inventions limits the initial electron flow in two ways:

The discharge current is minimized by the resistance R of the control circuit and inherent resistance of the mat. A resistance of approximately 10 meg ohms or greater has been determined to be sufficient to minimize these initial shock effects.

By segmenting or minimizing the size of the conductive surface the number of electrons in its contribution to the initial shock are also reduced. For example, experimentation with conductive vinyl mats indicates surfaces of 1–2 square feet exhibit much less shock perception than mats of 5 square feet.

This principle can be understood by referring to FIG. 11 of the parent application. A system is shown that includes a contact element, such as a mat that is electrically connected to a ground circuit by plugging a conductor into a grounded connection at a plug. The grounded connection is directly connected to earth which contains a large mass of electrons. The conductor itself, is a source of electrons. Thus, if a person who has built up an ESD charge touches the conductor, the mass of electrons in the ground and in the earth will be available for a shock to that person. A contact device can be a mat or any other object that is likely to be touched by a user. If the contact device is isolated from any mass of electrons, the person touching that device will not receive a shock. However, if there is any mass of electrons available, even if the mass is associated only with the conductor, the person is likely to receive a shock upon touching the device. However, if the device is not electrically connected to some mass of electrons, the person touching the device will not discharge the electrostatic energy he or she has built up. Therefore, there is a double-edge sword present: there must be some mass of electrons available so a discharge can be effected; however, the mass of electrons must not be so large that a painful shock is felt upon the discharge occurring.

Realizing this, the present invention electrically connects a contact device to a source of electrons, but does so in a manner that keeps the mass of electrons available to a minimum. The invention achieves this result by placing a resistor, such as resistor ER, physically close to the contact point so some electron current is available, but not as large a current as might be present if the wire itself is present in the discharge circuit. Heretofore, no one has realized that the wire itself might be a source of electrons that produce a shock during ESD.

The resistor being physically close, in some cases, within one foot, to the contact point reduces the current available to discharge the electrostatic charge on a person. Since the current is reduced, the discharge will be slower than if a large mass of electrons versus time is available. Thus, the present invention accounts for this by creating a situation where the person contacts the discharge contact on a continuous basis for long periods of time as compared to a few microseconds. The "slow" slight discharge is nearly, if not totally, unnoticed by the person yet is extremely effective in achieving the ultimate purpose of bleeding the ESD from a person in a non-noticeable manner.

The objects of this invention are achieved by a system which provides for augmenting the ESD grounding of various desired surfaces including flooring systems such as anti-static carpet without out the trauma of reinstallation and, if desired, to achieve a single point ground source for best equipotential protection of the user and/or equipment. The equipotential is important because the person in the workplace may, for example, be wearing headphones which are eventually connected to ground capable of grounding ESD. If the flooring or other items such as a monitor face plate were not grounded to the same source shocks might result through the ear. This has become somewhat common in the workplace and is traumatic to the person.

For the discussion below, the term carpeting will be used. However, it is understood that other floorings, mats, etc are implied.

Referring first to FIG. 1A, a basic circuit 10 is shown as including a contact element 12 that is in electrical contact with a floor covering 14, such as a floor mat, carpeting, or the like, and which is connected to a circuit 16 by a conductor 18. Circuit 16 will be discussed in greater detail below, and is electrically connected to ground 20 by a conductor 22. A plug 24, such as disclosed in the co-pending and parent applications, can be used to connect conductor 22 to ground 20.

Ground 20 may be a grounded object or the service entrance ground of a building via ground wiring. Contact element 12 can be either between floor covering 14 and a floor or can be located on top of that floor covering as will be understood from the teaching of the present description.

Figure 1B:
FIG. 1B is a schematic illustrating one form of the circuit of the present invention.
Figure 1C:
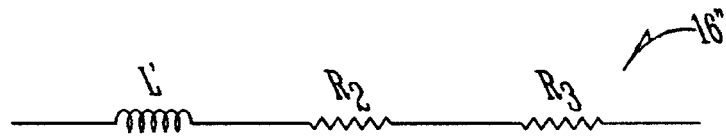
FIG. 1C is a schematic illustrating another form of the circuit of the present invention.

Two forms of circuit 16 are indicated in FIGS. 1B and 1C as circuits 16' and 16" respectively. Circuit 16' includes a resistance $R_1$ and an inductor L. The values of these elements are discussed above and in the incorporated documents and thus will not be discussed again here circuit 16" includes an inductor L' in series with two resistors $R_2$ and $R_3$ with the value of resistor $R_2$ being that required for safety as discussed above and in the incorporated documents, and resistor $R_3$ being optional.

Figure 1D:
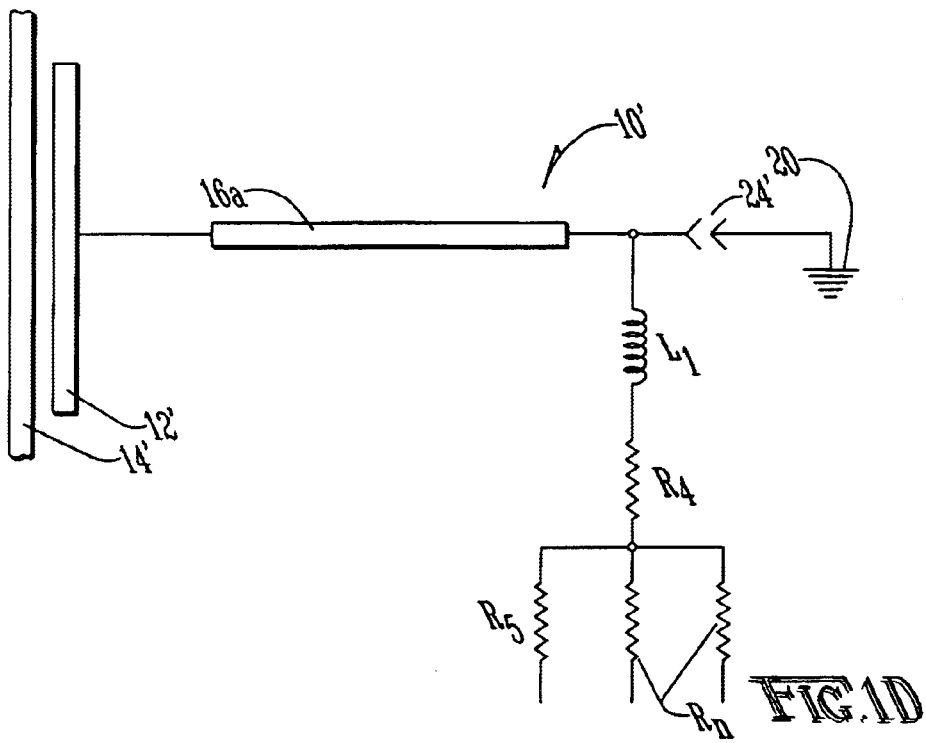
FIG. 1D is a schematic illustrating another form of the circuit of the present invention.

FIG. 1D shows a system 10' which accommodates multiple contact elements such as contact element 12' in electrical contact with a floor covering 14'. It is noted that contact element 12' could be a wrist strap or the like, and more than one contact element can be included in circuit 10'. Circuit 10' includes a circuit 16a which can be any of the above-discussed circuits and which electrically connects contact element 12' to ground 20. A plug 24 can also be included in circuit 10' if desired. Circuit 10' further includes inductors, such as inductor $L_1$ electrically connected to resistors, such as resistors $R_4$ which provide high frequency protection and safety respectively while resistors $R_5$ to $R_n$ electrically connect the individual contact elements to each other and provide electrical isolation between them. Resistors $R_5$ to $R_n$ are connected either directly to ground or to plug 24 via inductor $L_1$ and resistor $R_4$. Examples of values of the resistors are twenty megohms which would allow proper ESD performance but would not reflect an operator charge from one contact element to another.

Figure 2:
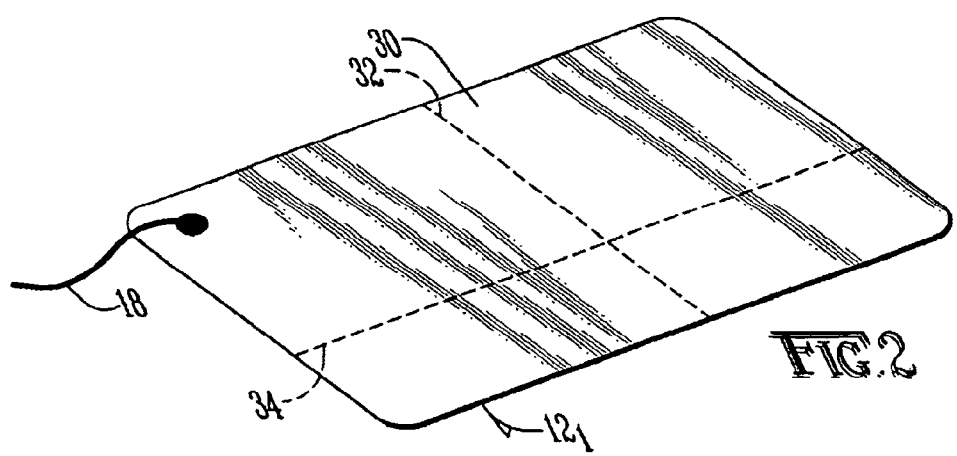
FIG. 2 is an insert to be placed under a floor covering.

Various forms of contact elements are shown in FIGS. 2–10. Thus, a contact element $12_1$ is shown in FIG. 2 as including a rectangular body 30 that is adapted to be installed between a floor covering, such as a carpet or a mat or the like, and the floor. Contact element $12_1$ can be installed by cutting a slot in a carpet and sliding contact element $12_1$ through the slot. Contact element $12_1$ is formed of thin conductive metal and is connected to circuit 16 by conductor 18. Perforations 32 and 34 can be provided to permit body 30 to be folded or cut for easing the insertion of the body through a slit in a carpet. In this manner, a large contact element can be placed beneath an existing floor covering without requiring a large slit to be defined through the floor covering.

Figure 3:
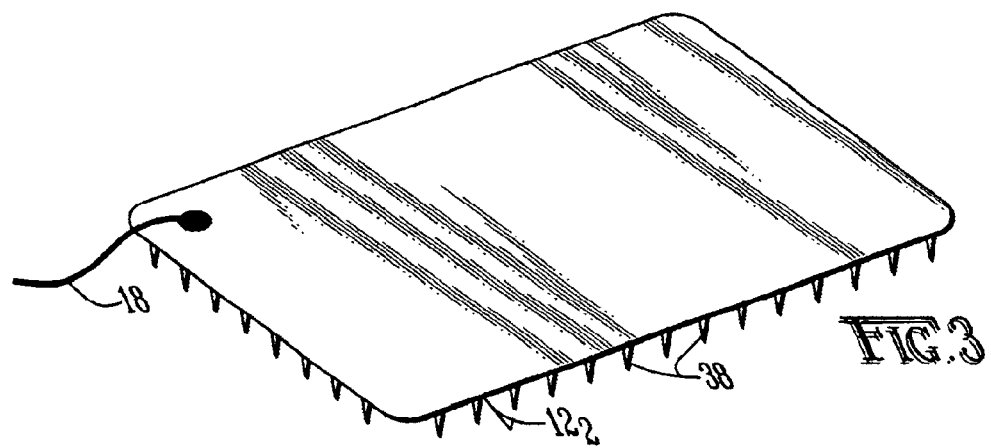
FIG. 3 is an insert to be placed on top of or under a floor covering.

FIG. 3 shows a contact element $12_2$ having floor covering engaging elements, such as teeth 38 which increase contact conductivity with the floor covering. An example of a contact element such as contact element $12_2$ would be a foot plate located under a filing cabinet, a computer or a bookcase or the like to achieve pressure for good contact to the floor covering. If the floor covering is multilayer with, for example a conductive backing, the teeth can provide connection to the conductive layer.

Figure 4A:
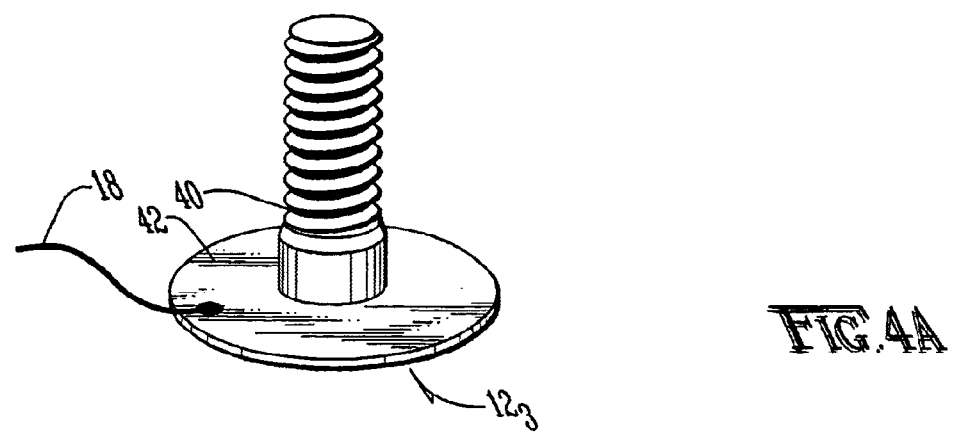

FIG. 4A shows a contact element $12_3$ which is a replacement foot for furniture, such as a leveling foot used on desks, modular office sections, chairs or the like. Contact element $12_3$ includes a threaded body 40 having a head 42 on one end thereof and which is connected to conductor 18 in the manner discussed above. Contact element $12_3$, like the other contact elements, is formed of electrically conductive material.

Figure 4B:
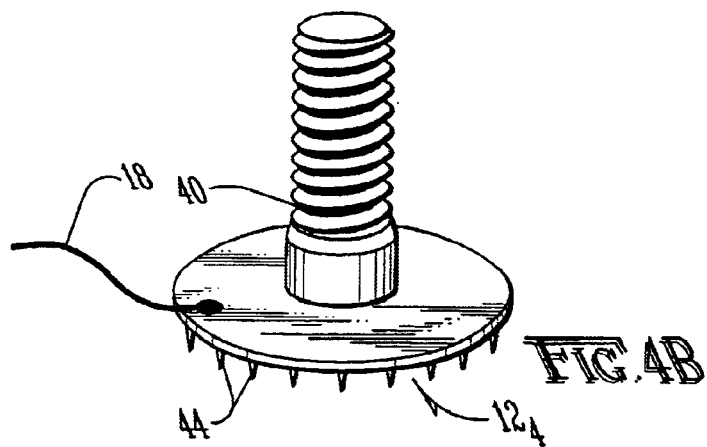

Contact element 124 shown in FIG. 4B is similar to contact element $12_3$ except contact element $12_4$ includes floor covering engaging elements, such as teeth 44. To facilitate adjustment, screw thread portion 40 may rotate independently of conductor 18 and be equipped with flat sided portions to allow adjustment (rotation) with a wrench or other tool, or conductor 18 may include a snap arrangement that is connected after any necessary rotation. In such a case, the contact portions may have a concave portion in the upper surface to enhance stable placement under an existing leveling foot.

Figure 5:
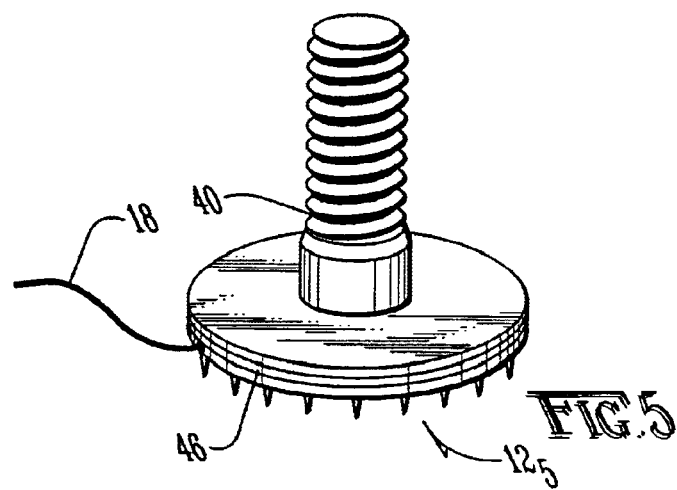

Contact element $12_5$ shown in FIG. 5 is similar to the just-discussed contact element $12_4$ but includes a layer of insulation 46 inserted into the contact element so that the ESD ground path will only be that provided by conductor 18 should the receptacle for the contact element be grounded. Although not shown in all figures, an insulating layer could be added to any of the other contact elements if desired. It is also noted that the threaded body of the contact elements can be omitted, resulting in a configuration similar to a furniture cup which could be inserted under other feet or legs of furniture.

Figure 6:
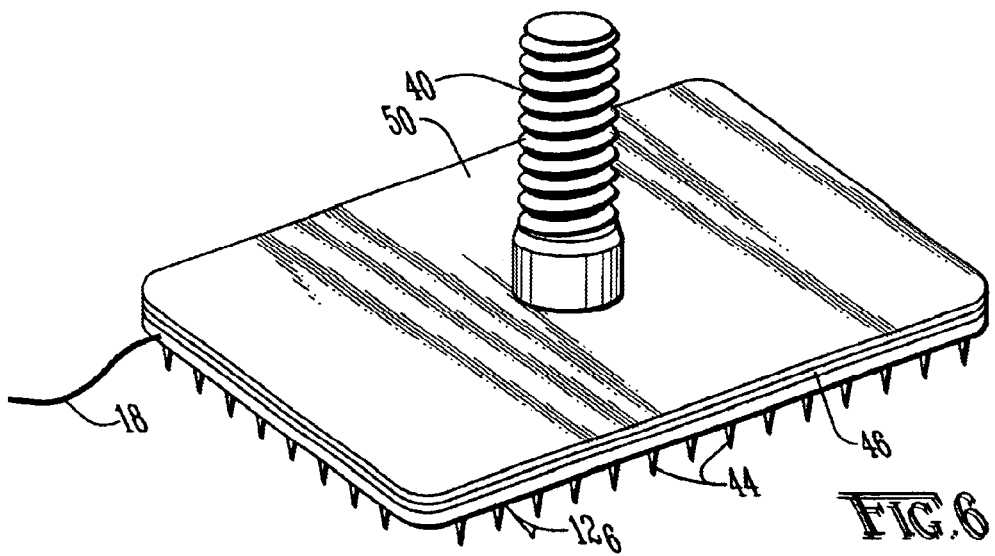
FIG. 6 is a rectangular insert to be placed on top of a floor covering or as a replacement as a foot for allowing more contact area than the original item provided.

Contact element $12_6$ shown in FIG. 6 includes a rectangular body 50 and can be placed beneath long structures as desired to increase contact area based upon the environment. For example, modular office furniture sections may have a panel extending for at least two feet on either side of a support foot. An elongated contact element such as contact element $12_6$ can be one inch wide by twenty inches long and could be used without being in the way by keeping the long dimension parallel to the panel.

Figure 7:
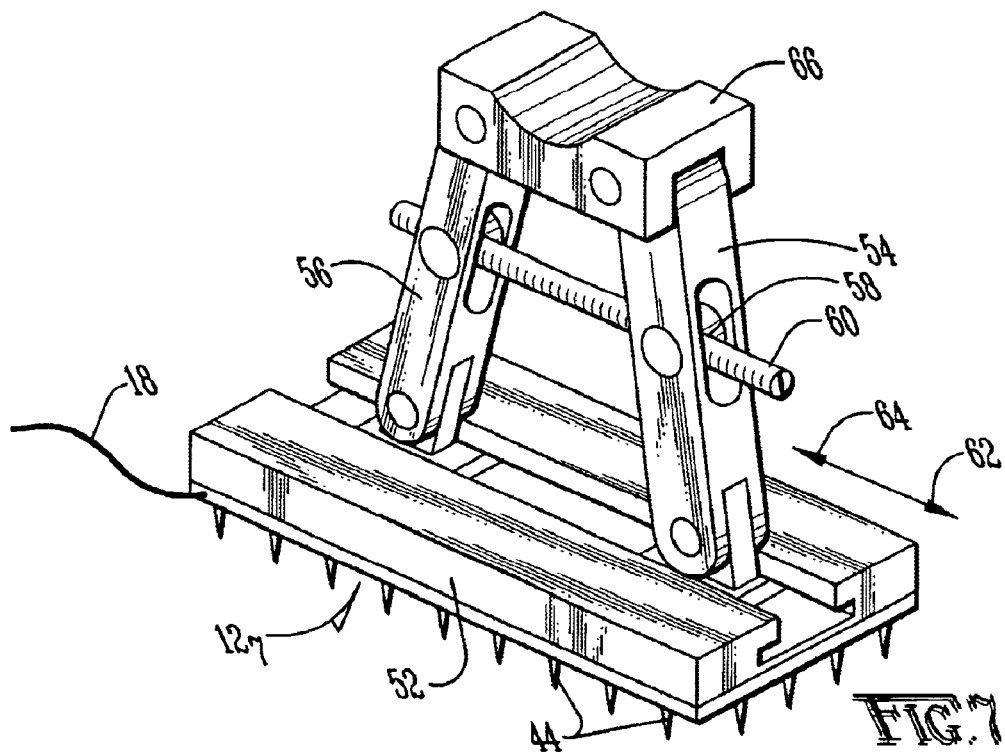
FIG. 7 is a wedge shaped insert to be placed on top of floor covering with floor covering engaging elements and engaging movable walls such as modular office partitions.

FIG. 7, shows a contact element $12_7$ as being wedge shaped with a base wall 52 having floor covering engaging elements 44 thereon and two side walls 54 and 56 extending upwardly therefrom to form a wedge shape. Each side wall has a threaded bore, such as threaded bore 58 in side wall 54 through which a threaded fastener 60 extends. Wall 54 is slidably mounted on base 52 to move in directions 62 and 64 as indicated by the double-headed arrow shown in FIG. 7. A top wall 66 connects walls 54 and 56 and is electrically conductive or insulated as desired as are the walls and base of the contact element. Contact element $12_7$ is connected to circuit 16 by conductor 18. Contact element $12_7$ can be wedged into the floor covering via gaps existing above the floor covering such as a modular floor panel sitting one inch above the floor covering with top wall 66 in contact with the panel or other device and base 52 in contact with the floor covering. Moving wall 54 changes the height of contact element $12_7$ to account for gap sizes and still ensure good contact between the floor covering and the element being supported on top wall 66.

Figure 8:
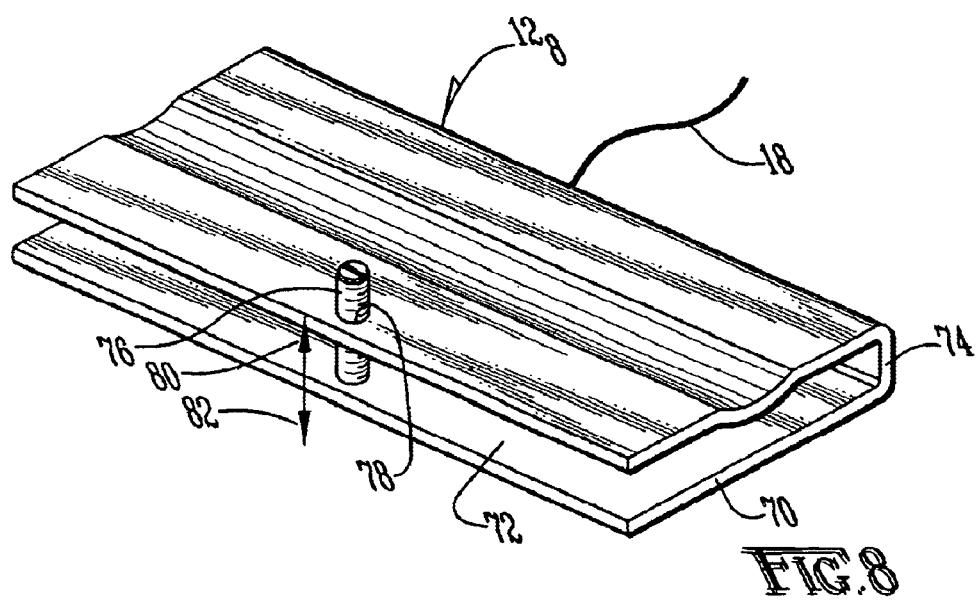
FIG. 8 is an insert to be placed on top of floor covering and engage an object spaced above the floor such as modular office movable walls.

Contact element $12_8$ shown in FIG. 8 is used for the same purpose as contact element $12_7$ and includes a base wall 70 and a top wall 72 connected together by a side wall 74. As in the case of contact element $12_7$, all of the walls are conductive or insulated as desired and a threaded stud 76 which is fixed to base wall 70 and is treatably received through a threaded bore 78 to move top wall 76 toward and away from base wall 70 in directions 80 and 82 shown by the double-headed arrow in FIG. 8. Contact element $12_8$ is connected to circuit 16 by conductor 18.

Figure 9:
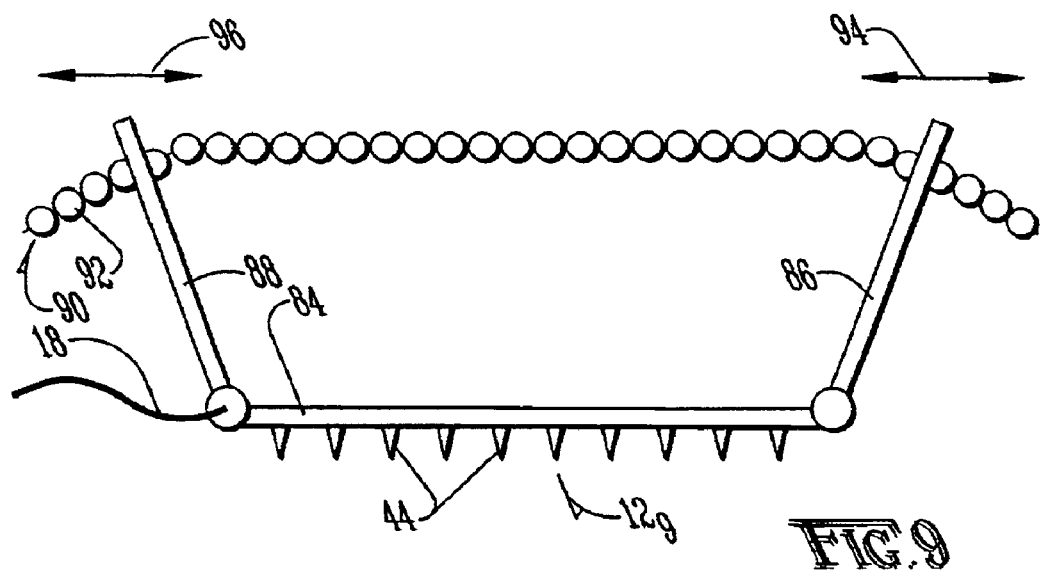
FIG. 9 is an insert to be placed in a space under an office partition and which has movable walls and floor covering engaging elements.

Contact element $12_9$ shown in FIG. 9 includes a base wall 84 and two side walls 86 and 88 which are coupled together by a chain 90 that extends through chain-accommodating holes defined through the walls. The chain includes balls, such as ball 92, that engage the walls adjacent to the chain-accommodating holes to hold the walls in the desired orientation with respect to each other. The walls move toward and away from each other as indicated by double-headed arrows 94 and 96. Moving the walls changes the height of contact element $12_9$ for the purposes discussed above. Floor covering engaging elements 44 are located on base wall 84, and a conductor 18 electrically connects contact element $12_9$ to circuit 16.

Figure 10:
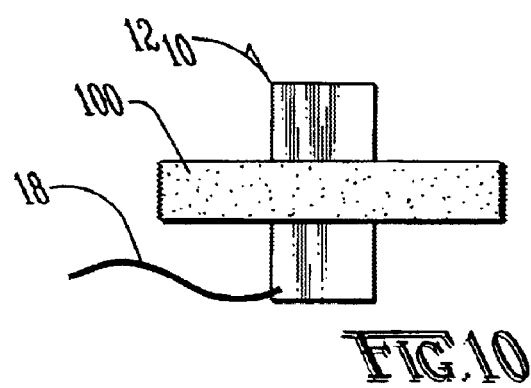
FIG. 10 is a general purpose contact element that can be adhered to a CRT face plate or other desired surface.

Contact element $12_{10}$ shown in FIG. 10 is a small contact plate that can be held on the face of a CRT monitor by tape 100 and is connected to circuit 16 by conductor 18.

The invention encompasses a number of grounding means to compensate for the potential lack of grounding to selected carpeting or flooring and to other devices such as CRT monitor faceplates. Contact to the carpeting or flooring is made by a relatively large conductive surface. This may be from the top of the carpeting with contact conductivity further enhanced by optional prongs penetrating into the carpet backing. It may also be from under the carpeting by either lifting a carpet tile if applicable or cutting a slit in the carpet to permit a contact element to be slipped under the carpet.

The shapes and sizes of the contact plate may change to be compatible with the available space and furniture configurations. The weight of furniture items may also be employed to provide pressure for a more intimate contact between the grounding element and carpet.

This discussion has used the words 'conductivity' and 'dissipative'. In the strict sense of ESD definitions they represent different resistance ranges. However, for the present purposes, the two may be used interchangeably. Dissipative typically refers to a resistance (conductivity) of approximately up to 1000 megohms. This may be viewed as setting an upper boundary for the total resistance of the circuit in this discussion (including the resistance of the flooring to charged object). Thus, the contact means of this invention can exhibit significant resistance, even in megohms, and still be effective (or a virtual short circuit) for purposes of draining ESD. This suitability of high resistance may also permit effective ESD protection on a short distance basis by some floorings not designed specifically for anti-static applications. For example, the means of this invention installed in a particular modular furniture cubical with conventional carpeting may provide ESD protection for a person resident in that particular cubical. Higher values of resistance can be used to an advantage to limit the current induced in a common ground system as discussed above. For example, consider an electrostatic voltage of 20,000 volts and a total path resistance 80 megohms. Maximum initial discharge current would be only 0.25 milliamps. Further reduction of the initial current can be achieved by including an inductor in the circuit path to limit the initial current and reduce high frequency content. The result is a current that is induced back into the common ground system that is so minimal as to create virtually no possibility of disturbing or damaging attached sensitive electronics.

As a lower boundary to resistance values safety must be considered. For example, if the ground wiring become exchanged with 120 volt AC wiring, there should be at least one megohm of series resistance present a all times to limit the current a person might receive to a low, safe value.

Various connection means are possible. A connection could be made to an existing ground screw on a receptacle. However, in many applications today, such as modular furniture there generally is no ground screw available. A special plug as fully described in a copending application which is incorporated herein by reference may be constructed to provide access to the building third wire AC power ground. This plug may also contain as a series element of at least the resistance described above to provide safety and the inductor described above. A connection means is provided to connect to one or more of the contact elements described in this invention. Resistance beyond the minimum for safety may be included on the plug or distributed among the contact device connections. The plug may also include a test circuit to verify correct polarities and grounding or other parameters as desired. Other variations will be obvious to one skilled in the art based on the teaching of this disclosure.

Due to a wiring error 120 volts AC might be inserted in place of the grounding conductor, or the person may come in contact with 120 volts. Therefore a minimum resistance, for example 1 megohm or another value as applicable for the particular voltage exposure should be maintained to insure an minimal low safe fault current under those conditions.

Figure 12:
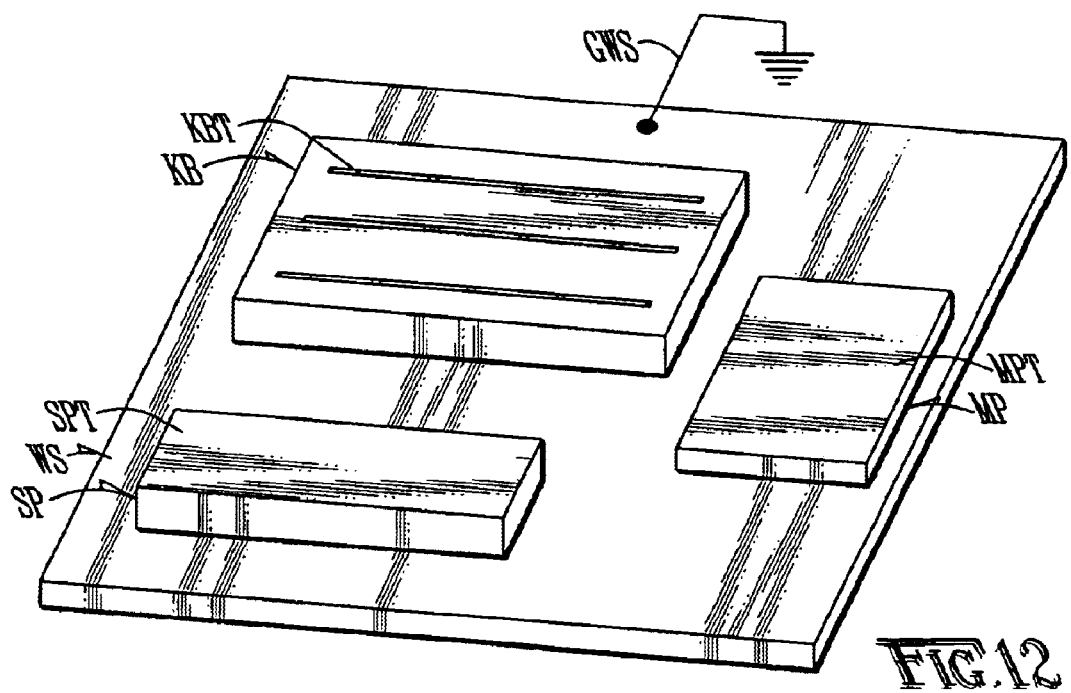
FIG. 12 shows an ESD protection system in which equipment is layered on an ESD grounded work surface.

The teaching of the present invention can be applied to a situation in which equipment, such as computer accessories or the like, can be grounded without significantly altering this equipment. Referring to FIG. 12, it can be seen that an ESD work surface WS is grounded via circuit GWS, which has been fully disclosed in co-pending patent application titled A PLUG AND CIRCUITRY FOR GROUNDING AN ELEMENT, the disclosure of which is fully incorporated herein by reference. Accordingly, the operation and function of the grounding circuit will not be discussed herein. The elements to be grounded shown in FIG. 12 include a mouse pad MS, and/or a wrist support SP, and/or a keyboard KB. Other elements can be used in place of the elements shown in FIG. 12 as will occur to those skilled in the art based on the teaching of the present disclosure, and such elements are intended to be included in the present invention as well.

Figure 13:
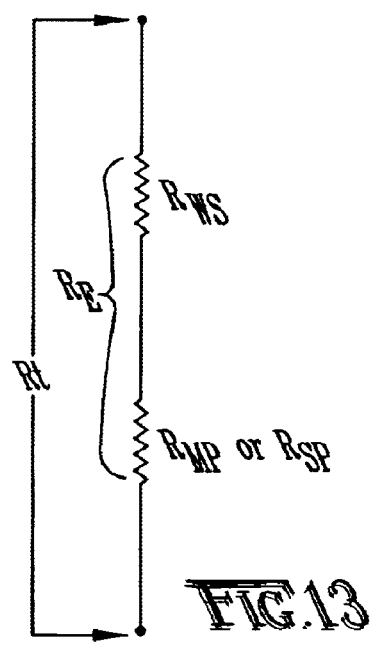
FIG. 13 is a schematic illustrating the resistances associated with the layered form of the invention shown in FIG. 12.

The elements to be ESD grounded simply rest on and are supported on the work surface and are in electrical contact with work surface WS. Referring to FIG. 13, it can be understood that the total resistance to the user $R_t$ is defined by the addition of series resistances $R_{WS}$ associated with the work surface WS plus $R_E$. Resistance $R_E$ is a sum of the resistance $R_{WS}$ plus the resistance associated with the elements layered on top of the work support. In the case shown in FIG. 12, $R_E$ is $R_{WS}$ plus $R_{MP}$ which is the resistance associated with the mouse pad resting on the work surface, or $R_E$ is $R_{WS}$ plus $R_{SP}$ which is the resistance associated with the wrist support resting on the work surface. Other resistances associated with other elements will be handled in the same manner as just discussed.

The materials used in any of the elements, including the work surface, are selected such that $R_E$ is conductive or dissipative in ESD terms from the top surface contacted by the user, such as surface SPT or surface KPT or MPT to through the ground circuit GWS. The ESD conductive and/or ESD dissipative values are discussed above and in the incorporated documents and reference is made thereto for such discussion. Since there are no wires on the elements layered on the work surface, these elements may be located anywhere on the work surface.

Figure 11A:
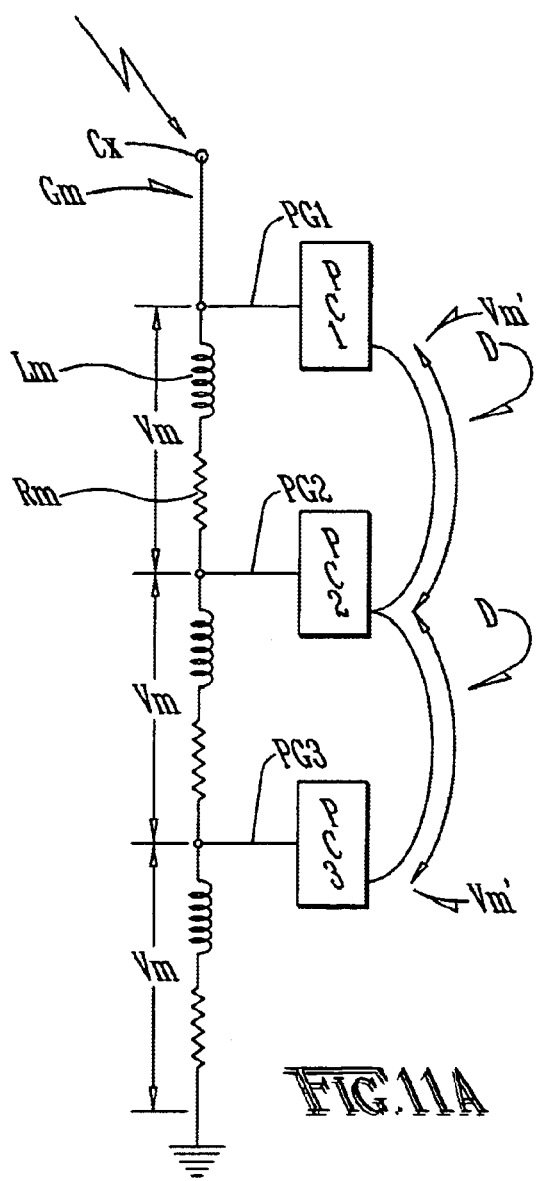
FIG. 11A is a schematic illustrating a prior art disruptive signal sneak path caused by prior art improper grounding.
Figure 11B:
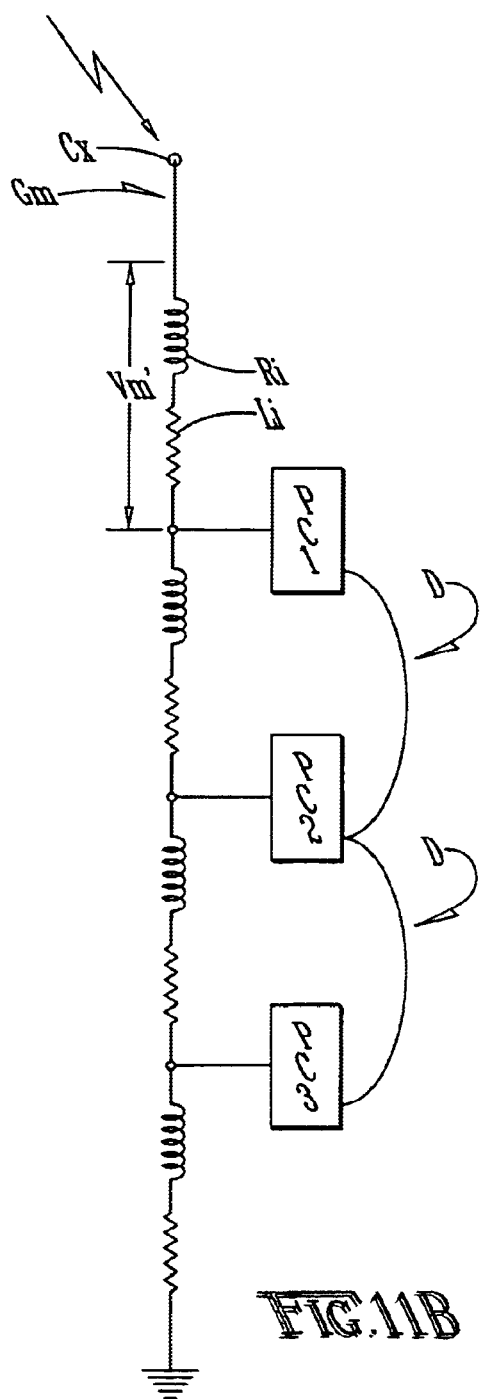
FIG. 11B is a schematic illustrating controlled sneak paths with reduced or eliminated disruptive sneak path voltages or currents due to the use of the ESD grounding circuits embodying the teaching of the present invention.

FIGS. 11A and 11B illustrate a typical PC computer network with PC1, PC2 and PC3 tied together by network data cables D. Ground wires PG1, PG2 and PG3 connect each computer chassis to main ground as shown as ground wire Gm via the power plugs. All ground wires have resistance and inductance as shown by Rm and Lm. Cx in FIG. 11A represents an ESD event discharge of current into the ground wire. The ESD current causes voltages shown as Vm. This causes a related voltage Vm to appear access the data cables D and to be impressed on each PC leading to errors or damage.

In FIG. 11B, the ESD path includes resistance Ri and inductance Li. This is a series impedance described elsewhere in this and the co-pending applications. The diescharge voltage effectively appears across this impedance as Vm' since this impedance is considerably higher than the impedance of the power line. Thus, effectively no ESD voltage shows up across the network PCs.

It is understood that while certain forms of the present invention have been illustrated and described herein, it is not to be limited to the specific forms or arrangements of parts described and shown.

What is claimed is:

1. A system for protecting a person from surprise or uncomfortable electrostatic discharge (ESD) comprising:
   A) flooring material;
   B) a contact element in electrical contact with said flooring material;
   C) an electrical circuit in electrical communication with said contact element and including an electrical resistor having a resistance of at least one megohm; and
   D) a ground in electrical communication with said contact element via said electrical circuit.

2. The system defined in claim 1 wherein said electrical circuit includes an inductor.

3. The system defined in claim 1 further including a plug electrically connecting said electric circuit to said ground.

4. The electrical circuit defined in claim 2 further including a second electrical resistor.

5. The electrical circuit defined in claim 4 wherein said second resistor has a value of at least one megohm.

6. The electrical circuit defined in claim 4 further including a second contact element spaced from said contact element with said second resistor electrically located between said contact element and said second contact element.

7. The electrical circuit defined in claim 1 wherein said flooring includes a carpet-like covering.

8. The electrical circuit defined in claim 7 wherein said contact element includes elements that electrically engage said flooring.

9. The electrical circuit defined in claim 8 wherein said contact element is mounted on a foot for furniture.

10. The electrical circuit defined in claim 1 further including an electrical connector electrically connecting said contact to said ground and wherein said contact element further includes electrical insulation that is placed on said contact element in a manner so that an ESD ground path is only via said electrical connector between said contact and said ground.

11. The electrical circuit defined in claim 1 wherein said contact includes two walls and an adjustable connection between said two walls.

12. A system for protecting a person from surprise or uncomfortable electrostatic discharge (ESD) comprising:
    an electrostatic discharge conducting contact element which is in time-extended contact with a person who is to be protected from electrostatic discharge when in use, said time-extended contact being located in a floor covering;
    a control circuit electrically connected to said contact element, said control circuit including a first resistor element having a resistance which upon initial contact between the person and said contact element will drain some, but not all, ESD from said contact element;
    an inductor in series with said contact element;
    a ground circuit electrically associated with said control circuit.

13. A system for protecting a person or equipment from undesirable electrostatic discharge (ESD) comprising:
    A) a contact element in electrical contact with a floor covering;
    B) an electrical ground; and
    C) a circuit electrically connecting said contact element to said electrical ground.

14. The system defined in claim 13 wherein said circuit includes a resistor.

15. The system defined in claim 14 wherein said circuit further includes an inductor.

16. The system defined in claim 15 wherein said circuit further includes a second contact element.

17. The system defined in claim 16 further including a second resistor electrically interposed between said contact element and said second contact element.

18. The system defined in claim 17 wherein said circuit includes an inductor.

19. The system defined in claim 13 wherein said contact element includes a conductive metal sheet.

20. The system defined in claim 19 further including perforations defined in said contact element.

21. The system defined in claim 13 wherein said contact element includes floor covering engaging elements.

22. The system defined in claim 13 wherein said contact element includes a threaded body and a head on said threaded body.

23. The system defined in claim 22 wherein said contact element further includes floor covering engaging elements.

24. The system defined in claim 13 wherein said contact element further includes insulation.

25. The system defined in claim 24 wherein said contact element further includes floor covering engaging elements.

26. The system defined in claim 23 wherein said contact element further includes insulation.

27. The system defined in claim 13 wherein said contact element includes a rectangular body.

28. The system defined in claim 19 wherein said contact element includes floor covering engaging elements.

29. The system defined in claim 13 wherein said contact element includes two walls and an adjustable connection between said two walls.

30. A system for protecting equipment from electrostatic discharge (ESD) comprising:
A) flooring material;
B) a contact element in electrical contact with said flooring material;
C) an electrical circuit in electrical communication with said contact element and including an electrical resistor having a resistance of at least one megohm; and
D) a ground in electrical communication with said contact element via said electrical circuit.

31. A system for protecting equipment from electrostatic discharge (ESD) comprising:
an electrostatic discharge conducting contact element which is in time-extended contact with equipment that is to be protected from electrostatic discharge when in use, said time-extended contact being located in a floor covering;
a control circuit electrically connected to said contact element, said control circuit including a first resistor element having a resistance which upon initial contact between the equipment and a person will drain some, but not all, ESD from said contact element;
an inductor in series with said contact element;
a ground circuit electrically associated with said control circuit.

32. A system for protecting equipment from undesirable electrostatic discharge (ESD) comprising:
A) a contact element in electrical contact with a floor covering;
B) an electrical ground; and
C) a circuit electrically connecting said contact element to said electrical ground.

33. A system for protecting a person from surprise or uncomfortable electrostatic discharge (ESD) comprising:
A) flooring material;
B) a contact element in electrical contact with said flooring material;
C) an electrical circuit in electrical communication with said contact element; and
D) a ground in electrical communication with said contact element via said electrical circuit.

34. The system defined in claim 33 wherein said contact element includes a replacement foot for a furniture element.

* * * * *